US008172997B2

(12) United States Patent
Seal et al.

(10) Patent No.: US 8,172,997 B2
(45) Date of Patent: May 8, 2012

(54) CERIUM OXIDE NANOPARTICLE REGENERATIVE FREE RADICAL SENSOR

(75) Inventors: Sudipta Seal, Oviedo, FL (US); Hyoung Cho, Oviedo, FL (US); Swanand Patil, Orlando, FL (US); Anjum Mehta, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 887 days.

(21) Appl. No.: 11/915,697

(22) PCT Filed: May 26, 2006

(86) PCT No.: PCT/US2006/020472
§ 371 (c)(1),
(2), (4) Date: Oct. 3, 2008

(87) PCT Pub. No.: WO2006/130473
PCT Pub. Date: Dec. 7, 2006

(65) Prior Publication Data
US 2009/0071848 A1 Mar. 19, 2009

Related U.S. Application Data

(60) Provisional application No. 60/685,170, filed on May 27, 2005.

(51) Int. Cl.
*G01N 27/327* (2006.01)
(52) U.S. Cl. .................... 204/406; 205/792
(58) Field of Classification Search .......... 204/403.01–403.15; 205/777.5, 205/778, 792, 782, 789
See application file for complete search history.

(56) References Cited

U.S. PATENT DOCUMENTS

| 5,411,647 | A | 5/1995 | Johnson et al. |
| 6,042,714 | A | 3/2000 | Lin et al. |
| 6,139,985 | A | 10/2000 | Borglum et al. |
| 6,592,746 | B1 | 7/2003 | Schmid-Schoenbein et al. |

FOREIGN PATENT DOCUMENTS
WO 99/15891 4/1999

OTHER PUBLICATIONS

Dong et al. Activation of glassy carbon electrodes by dispersed metal oxide particles, J. Electrochem Soc., 1984, 813-819.*
Buettner et al. Ascorbate (Vitamin C), its Antioxidant Chemistry, Presentation.*

\* cited by examiner

*Primary Examiner* — Alex Noguerola
*Assistant Examiner* — Gurpreet Kaur
(74) *Attorney, Agent, or Firm* — Jetter & Associates, P.A.

(57) ABSTRACT

An electrochemical sensor system for sensing free radicals or materials which generate free radicals in solution includes a working electrode coated with a plurality of cerium oxide nanoparticles and a counter electrode. A solution to be analyzed provides electrolytes to electrically couple the working electrode to the counter electrode. Electronics are connected to at least one of the working and counter electrodes for measuring and amplifying an electrical current signal generated by reduction or oxidation occurring at the working electrode, wherein in a presence of free radicals an electrical current signal flows between the working electrode and the counter electrode. The system can be used to sense the presence of hydrogen peroxide.

16 Claims, 5 Drawing Sheets

A prototype device: (a) sensor electrode structure (b) nanoceria particles on working electrode

CERIUM OXIDE NANOPARTICLE REGENERATIVE FREE RADICAL SENSOR

CROSS REFERENCE TO RELATED APPLICATIONS

This is a U.S. National Phase application under 35 U.S.C. §371 of International Application No. PCT/US2006/020472, filed May 26, 2006 which claims the benefit of priority of U.S. Provisional Application Ser. No. 60/685,170 filed May 27, 2005. The International Application was published Dec. 7, 2006 as WO 2006/130473 under PCT Article 21 (2).

FIELD OF THE INVENTION

The present invention relates to electrochemical free radical sensors for fluids, and applications therefore, including the sensing of hydrogen peroxide ($H_2O_2$).

BACKGROUND OF THE INVENTION

Free radicals are highly reactive molecules having unpaired electrons in their outer electronic orbit. For example, hydrogen peroxide ($H_2O_2$) is an oxidizing agent which in the presence of organic matter, or if permitted to become alkaline, decomposes to oxygen and water. The dissociation reaction of hydrogen peroxide in an aqueous solution is as follows: $2H_2O_2 \sim 2H_2O + O_2$.

$O_2$ is a gas at standard temperature and pressure (STP). If this gas is present in solution, the gas has a valency of two. Accordingly, it has two spare electrons to form a bond with another element, such as oxygen, carbon or a metal. For example, molecular structure of $O_2$ is O═O. However at any given time a very small proportion of the oxygen in solution will dissociate to form free oxygen atoms O. However, these free oxygen atoms or radicals now carry a-ve charge and are extremely unstable. In effect they must combine with another oxygen free radical to form an oxygen molecule, or they will react with organic matter by splitting carbon double bonds, or with metals to form a metal oxide.

Hydrogen peroxide is found in natural water, such as sea water, or rain water, where it is an important species in redox reactions, in industrial processes, and in biological tissues, including blood, as a result of enzymatic reactions. Direct detection of hydrogen peroxide is an important analytical task, and numerous techniques have been devised for measurement of hydrogen peroxide levels in fluids as indications of medical conditions, environmental quality, or the presence of pathogens in cells of both animals and plants.

Superoxide radicals ($O_2.-$) in living tissue can be derived from many sources, such as activated granulocytes, endothelial cells, xanthine oxidase-catalyzed reactions, mitochondrial metabolism, and transition metal reactions with oxygen. Hydrogen peroxide ($H_2O_2$) can be produced from the dismutation of superoxide radicals ($O_2.$) catalyzed by the enzyme superoxide dimutase (SOD), from transition metal reactions with superoxide radicals, and from enzymes (e.g., glycollate oxidase and urate oxidase) which produce peroxide directly without first producing superoxide. The presence of antioxidants, including certain enzymes such as SOD and catalase, serves to limit the concentration of the reactive oxygen species in plasma and tissues. Therefore, an increase in either the production of free radicals and/or a decrease in antioxidants can cause oxidative stress, contributing to possible cardiovascular complications in animals and humans. Similarly, oxygen free radicals may affect vascular resistance by inactivating nitric oxide (NO), thereby causing arteriolar vasoconstriction and elevation of peripheral hemodynamic resistance. Other conditions have also been associated with oxidative stress, including arthritis, acceleration of the progression of HIV to full-blown AIDS, and neurological diseases such as ALS.

Oxygen free radicals and related intermediates have also been suggested as playing a role in hypertension and may play a role by affecting vascular smooth muscle contraction and resistance to blood flow. In individuals with histories of conditions such as atherosclerosis, stroke and myocardial infarction, hypertension constitutes a risk factor.

A number of different techniques are known for measurement of oxygen free radicals and their intermediates. These methods include the use of electrodes, chemiluminescence, and fluorescence. These methods are all limited to measuring oxygen free radicals from stimulated neutrophils or deproteinized whole blood.

A hydrogen peroxide sensing system for measuring hydrogen peroxide in plasma is disclosed in published PCT patent application No. WO/1999/015891 entitled "SYSTEM AND METHOD FOR MEASURING HYDROGEN PEROXIDE LEVELS IN A FLUID AND METHOD FOR ASSESSING OXIDATIVE STRESS," inventors Lacy et al. In the disclosed system the test sample of plasma from a fluid or fluid-containing material which is to be analyzed for hydrogen peroxide content is divided into two equal portions and a hydrogen peroxide oxidation sensor is inserted into each portion. An inhibitor for the enzyme catalase, such as sodium azide, is added to one of the portions to stabilize the hydrogen peroxide present. A quantity of catalase is added to the other portion to deplete any hydrogen peroxide present by catalyzing it to oxygen. Hydrogen peroxide oxidation of each portion at the respective sensor is then measured, along with background oxidation of any other oxidizable species in the sample. The signal from the sensor in the depleted hydrogen peroxide sample is subtracted from the signal from the stabilized hydrogen peroxide sample to eliminate the signals' contributions from background oxidation, thus yielding a resultant signal which is representative of the amount of hydrogen peroxide production in the subject fluid or material.

While the system disclosed in WO/1999/015891 may have limited utility in certain applications, it requires two separate portions of the plasma from the sample fluid or material as well as chemical treatment of each of the portions. Such a system is useful primarily in a laboratory where there are facilities for chemically treating the portions, and where supplies of the treating chemicals can be made available. This disclosed system is not particularly useful for analysis of samples in the field or where the treating chemicals are not conveniently available. This system also does not account for the fact that either or both of the treating agents may affect other components of the samples so that the two samples may end up being different from each other with respect to more than just the hydrogen peroxide component. Further, since the treating chemicals or enzymes must be added to each sample, the system must be recalibrated for each run.

U.S. Pat. No. 6,592,746 to Schmid-Schoenbein issued on Jul. 15, 2003 discloses a sensor probe for determining hydrogen peroxide concentration. The disclosed sensor probe can measure the hydrogen peroxide content of a single sample using two oxygen sensors whose electrodes are encased in defined membranes. The oxygen reference sensor is encased in a hydrophobic membrane which prevents the transport of hydrogen peroxide or electrochemical poisons or interferents and isolates the electrodes and an electrolyte fluid surrounding the electrodes from the sample fluid. The hydrogen-peroxide-generated oxygen (HPGO) sensor is also is encased in such a hydrophobic membrane, but has in series with and distally of the hydrophobic membrane a hydrophilic membrane which contains an immobilized enzyme such as catalase, peroxidase or other enzymes of a family which catalyzes the reaction of hydrogen peroxide to oxygen and water. At the HPGO sensor, the hydrogen peroxide is catalyzed to oxygen by the enzyme so that the HPGO sensor measures an enhanced concentration of oxygen relative to the oxygen reference sensor. The signals of each of the oxygen sensors are sent to a summer, which subtracts the equal background oxygen concentration of both, yielding a resultant difference signal representative of the concentration of hydrogen peroxide content of the sample itself. A suitable display or data collection device is used to capture the information in visible or digital form. Methods of use of the device for determining hydrogen peroxide content of human or animal tissues or fluids, or environmental or industrial fluids or fluid-containing materials, are also disclosed. Unfortunately, the immobilized enzyme-based probe disclosed by Schmid-Schoenbein have poor durability due to causes including the leaching of proteins during sensing. In addition, the enzyme-based probes require special care for storage, including generally low temperatures and wet conditions.

SUMMARY

An electrochemical sensor system for sensing free radicals or materials which generate free radicals in solution comprises a working electrode, the working electrode having a coating layer thereon comprising a plurality of cerium oxide nanoparticles. A counter electrode is provided wherein a solution to be analyzed provides electrolytes to electrically couple the working electrode to the counter electrode. Electronics are electrically coupled to at least one of the working and counter electrode for measuring and amplifying an electrical current signal generated by reduction or oxidation occurring at the working electrode.

The average size of the cerium oxide nanoparticles is generally between 2 and 20 nm, and in one embodiment between 2 and 8 nm. A thickness of the coating layer is generally between 40 nm and 1 μm. The coating layer can be porous. The cerium oxide nanoparticles can be doped with at least one trivalent element, such as La or Nd.

In another embodiment, the system further comprises an integrated circuit substrate, wherein the sensor is a MEMS sensor formed on the integrated circuit substrate. The substrate can comprise silicon. The system can include electronics on the chip, such as a potentiostat, coupled to the electrodes disposed on the chip.

An electrode for sensing free radicals or materials which generate free radicals in solution comprises an electrically conducting core material, such as Pt. The core has a coating layer thereon comprising a plurality of cerium oxide nanoparticles having an average size of between 2 and 20 nm. The cerium oxide nanoparticles can be doped with at least one trivalent element.

A method of sensing free radicals or materials which generate free radicals in solution comprises the steps of providing a sensor electrode for sensing free radicals or materials which generate free radicals in solution, comprising an electrically conducting core material, the core having a coating layer thereon comprising a plurality of cerium oxide nanoparticles having an average size of between 2 and 20 nm, and positioning the sensor electrode proximate to a solution or medium having an associated solution to be analyzed, the sensor electrode being electrically coupled to a counter electrode. The electrical current signal generated by reduction or oxidation occurring at the sensor electrode is measured, and a presence of free radicals in the solution or medium is determined based on the current signal. The medium can comprise human tissue. The material being sensed can comprise hydrogen peroxide. The method can comprise the step of determining a concentration of hydrogen peroxide based on the current signal.

BRIEF DESCRIPTION OF FIGURES

There is shown in the drawings embodiments which are presently preferred, it being understood, however, that the invention can be embodied in other forms without departing from the spirit or essential attributes thereof.

FIG. 1(a) shows a cerium oxide nanoparticle coated sensor electrode disposed in glass tubing according to an embodiment of the invention, FIG. 1(b) shows an amperometric free radical sensor system including the cerium oxide nanoparticle coated sensor electrode, while

DETAILED DESCRIPTION

Figure 1:
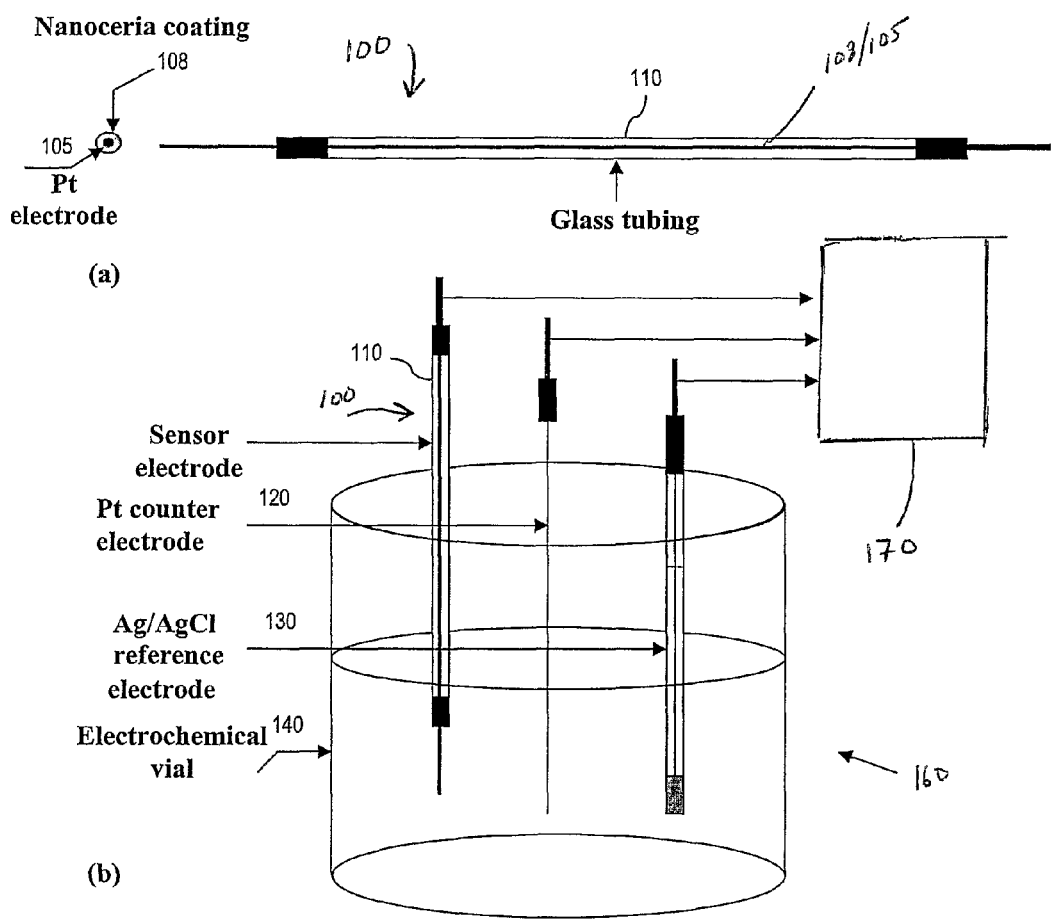

An electrochemical sensor for sensing free radicals or materials which generate free radicals in solution comprises a working electrode coated with a layer comprising a plurality of cerium oxide nanoparticles, and a counter electrode. An optional reference electrode is also preferably provided. An electrolyte couples the working electrode to the counter electrode. The electrolyte can be provided by the solution to be analyzed. Electronics are provided which are electrically coupled to at least one of the working and counter electrodes for measuring and amplifying an electrical current signal generated in the presence of free radicals by the reduction or oxidation which occurs at the working electrode in the presence of the free radicals.

As known by those having ordinary skill in the art, chemically, most of the rare earth (RE) elements (atomic numbers 57 through 71) are trivalent. Cerium alone is known to form compounds with a valence of +4, such as $CeO_2$ (ceria). Cerium is believed to be a unique material with regard to the mixed valence states provided, both +3 and +4. However, at least with regard to cerium oxide compounds, the vast majority of valence states are +4 states.

Cerium of valence +3 is generally referred to as cerous, while with valence +4 is generally referred to as ceric. Cerium oxide includes both ceric oxide and cerous oxide. Cerous oxide is also known as Cerium III oxide and has the formula $Ce_2O_3$. Ceric oxide is known as ceria, cerium dioxide and cerium IV oxide and has the chemical formula $CeO_2$.

The cerium oxide nanoparticles used with the invention have an average particle size <20 nm, such as in the range from 1 to 10 nanometers, for example 3 to 7 nm. The inventors have found that an average cerium oxide nanoparticle size in the range <20 nm provides an unexpected and highly beneficial result which is believed to be based on an increased percentage of +3 valence states (relative to the generally more numerous +4 states) on the cerium oxide nanoparticles surface. The increasing percentage of +3 valence states is believed to increase as the cerium oxide nanoparticle size decreases in this size range. The presence of a relatively high percentage of +3 valence states has been found to significantly improve performance of sensors according to the invention. A large relative percentage of +3 states in the <20 nm cerium oxide nanoparticles have also been found by the inventors to provide efficient regeneration as described below.

The thickness range for the cerium oxide nanoparticles layer is generally 100 to 300 nm, but can be thicker or thinner than this range, such as 20 nm to 1 μm. The cerium oxide nanoparticle layer can be porous. The surfactant used in the reverse micelle process described below helps keeps the cerium oxide nanoparticles separate to provide a porous layer. The cerium oxide nanoparticles can be doped using trivalent elements, such as rare earth elements, for example La and Nd, which may increase the concentration of vacancies. The concentration range for trivalent doping elements is generally up to about 40 wt %.

Ceria nanoparticles are presently available commercially in the average size range from about 7 to 20 nm. However, such particles are formed from a high temperature process which renders the ceria nanoparticles highly agglomerated. For use with the invention, cerium oxide nanoparticles particles are preferably obtained in a non-agglomerated state. A reverse-micelle process using unique reagents can be used to form substantially non-agglomerated cerium oxide nanoparticles for use with the invention. Such a process also provides cerium oxide nanoparticles having an average size down to about 2 nm.

A reverse micelle method according to the invention for preparing cerium oxide nanoparticles of the size approximately 2 to approximately 10 nm is described below. Those having ordinary skill in the art will realize that the method described is not limited to the specific concentrations or species disclosed. In one embodiment, the method can include the steps of dissolving approximately 0.5 to approximately 1.0 gm of the cerium oxide nanoparticle precursor $Ce(NO)_3.6H_2O$ in deionized water to make approximately 10 ml of solution to form a first solution. A second solution is then formed by dissolving approximately 3 gm to approximately 4 gm of the anionic surfactant AOT (sodium bis(2-ethylhexyl) sulphosuccinate) in approximately 200 ml of toluene. The first and second solutions are then combined and then stirred for approximately 30 min while drop wise adding approximately 30% $H_2O_2$ until the stirred combined solution becomes yellow, and subsequently stirring proceeds for approximately 30 to 60 min. Alternatively, the method can include adding $NH_4OH$ instead to $H_2O_2$. Other reverse micelle process may be used to form cerium oxide nanoparticles useful for the invention. For example, a reverse micelle process analogous to the process disclosed in U.S. Pat. No. 6,413,489 to Ying et al. may be used to form the highly non-agglomerated cerium oxide nanoparticles.

Ying discloses techniques for making very small particles of a variety of materials, small particles of material that can be made by the processing method, and methods of use of these particles. One aspect of Ying provides a method for preparing a particle. The method involves providing an emulsion having a water content of about 1-40% and includes a hydrocarbon and at least one surfactant. The emulsion forms micelles which comprise a disperse aqueous phase. At least one reactant is added which reacts in and with the disperse aqueous phase to form a particle having a particle size of less than about 100 nm where the particle is free from agglomeration. Another embodiment of Ying provides a method for preparing a particle from an emulsion having a water content of about 1-40% and includes a hydrocarbon and at least one non-ionic surfactant. The emulsion forms micelles which comprise a disperse aqueous phase. At least one reactant is added resulting in a particle having a particle size of less than about 100 nm where the particle is free from agglomeration.

Cerium oxide nanoparticles of a size approximately 2 nm to 20 nm in diameter can also be prepared by a process including the steps of dissolving approximately 0.5 grams to approximately 1.0 grams of $Ce(NO_3)_3 6H_2O$ in deionized water to make approximately 10 mls of solution to form a first solution, followed by dissolving approximately 3 grams to approximately 4 grams of AOT (surfactant) in approximately 200 ml of solvent to form a second solution, followed by combining the first and the second solutions, following by stirring the combined solutions for approximately 30 minutes, and drop wise adding approximately 30% hydrogen peroxide ($H_2O_2$) until the stirred combined solution becomes yellow, and subsequently stirring for approximately 30 minutes to approximately 60 minutes more.

The surfactant molecules are influenced by the water molecules to form micelles and changing the water and surfactant ratio can control the size of the micelles. The aqueous solution of rare earth metal salt is then confined to the nano-sized micelles of surfactant forming nano-reactors. When hydrogen peroxide is added to the solution, it penetrates the micelle to react with cerium nitrate to form ceria nano particles. The reaction is represented as follows in equation 1:

$$Ce(NO)_3 + H_2O_2 + H^+(aq) \rightarrow CeO_2 + 3HNO_3 \qquad 1.$$

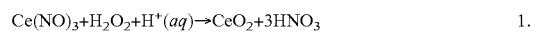

Hydrogen peroxide also converts $Ce^{3+}$ to $Ce^{4+}$ as shown below in equation 2:

$$Ce^{3+} + H_2O_2 + 2H^+(aq) \rightarrow Ce^{4+} + 2H_2O \qquad 2.$$

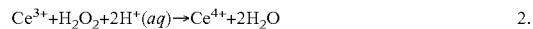

$Ce^{+4}$ is the most stable state, however, having a mix of $Ce^{+3}$ and $Ce^{+4}$ is generally good because the nanostructure will have many vacancies, which can initiate catalytic reactions. Most of the Ce ions are present on the surface of the nanoparticles, for example approximately 75% for an approximately 2.6 nanometer (nm) particle. Thus, many sites are available for surface chemical reactions for the Ce ions. Oxygen vacancies are generated by such surface chemical reactions. During the surface chemical reactions, oxygen atoms from the ceria surface are taken away leading to non-stoichiometry $CeO_{2-x}$.

Thus, aqueous reverse micelles (RMs) are surfactant aggregates in nonpolar solvents that enclose packets of aqueous solution in their interior. The size of the water droplet can be tuned by varying the ratio of water to surfactant. RMs used as reaction media in the production of nanoparticles who size and shape are controlled by water and surfactant ratio.

Unlike materials used for prior free radical sensors as noted in the background above, cerium oxide is chemically stable. Accordingly, there are generally no special requirements, such as low temperature or wet conditions, for storage of sensors according to the invention.

Applicants, not seeking to be bound to theory, present the following mechanism to explain the reactivity of cerium oxide nanoparticles towards free radicals and the basis of its regenerativity. As noted above, cerium oxide crystals include both $Ce^{+3}$ and $Ce^{+4}$ valence states. $Ce^{+4}$ ions are believed to reduce to $Ce^{+3}$ by extracting a free electron from a free radical, such as shown below:

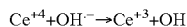

$$Ce^{+4} + OH^- \rightarrow Ce^{+3} + OH$$

The $Ce^{+3}$ ions can return to $Ce^{+4}$ by surface chemical reactions occurring at the cerium oxide surface. Regeneration process will be likely be faster in solutions/liquids as compared to regeneration in air. Thus, sensor systems according to the invention can be regenerative. Regeneration increases the usable lifetime of sensors according to the invention as compared to other sensors, such as protein modified sensors. The cerium oxide nanoparticle layer can also react with $H_2O_2$ to form the $Ce(OH)_3OOH$ complex. This complex has limited stability and tends to revert to its original state, thus again providing regeneration.

A catalyst is a chemical substance that accelerates a chemical reaction. Whenever oxygen in solution comes into contact with the surface of the catalyst, the catalyst can significantly increase the degree of dissociation, and hence the concentration of free radicals. Substances that can be used as catalysts with the present invention include metal oxides including manganese dioxide, iron oxide and titanium dioxide. The concentration range for the catalyst is up to about 10 wt. %, preferably being from about 5-10 wt %. The catalyst introduction process can be made compatible with the reverse micelle process described above by mixing the catalyst precursor with the cerium oxide precursor during cerium oxide nanoparticle synthesis.

Now referring to FIG. 1(a), electrode member 100 comprising a cerium oxide nanoparticle coated sensor electrode (working electrode) 108/105 disposed inside glass tubing 110 according to an embodiment of the invention is shown, while FIG. 1(b) shows an amperometric free radical sensor system 160 including electrode member 100. The electrode portion of electrode member 100 comprises cerium oxide nanoparticles 108 coating an inner Pt electrode 105. Although Pt is shown in FIGS. 1(a) and (b), other electrode materials may be used with the invention.

A Pt counter electrode 120 and Ag/AgCl reference electrode 130 are shown in FIG. 1(b). The respective electrodes are disposed in an electrochemical vial 140 filled with a solution to be analyzed for the presence of free radicals. The electrodes are connected to a measurement circuit 170.

Figure 1C:
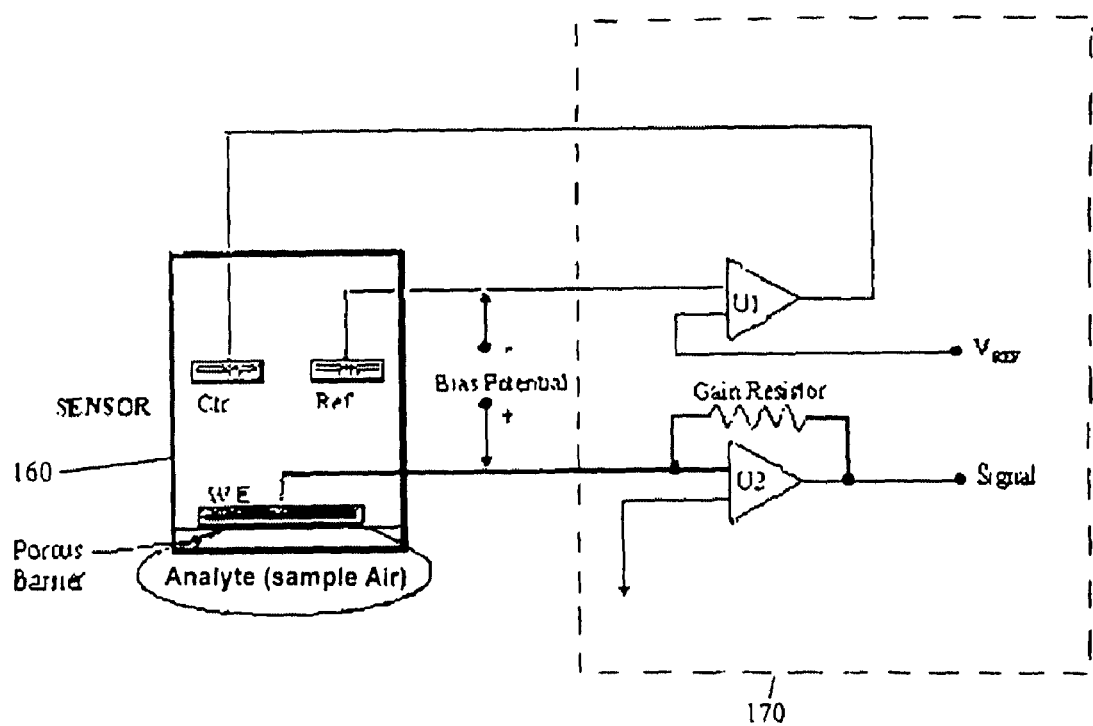
FIG. 1(c) shows an exemplary electrochemical sensor according to an embodiment of the invention coupled to a potentiostat circuit.

FIG. 1(c) shows a schematic of an exemplary electrochemical sensor according to an embodiment of the invention 160 coupled to a potentiostat circuit 170. The potentiostat circuit controls the potential of the working electrode and converts the sensed signal current from the working electrode (WE) to a voltage. This signal current is converted to a voltage by operational amplifier U2. This circuit 170 also maintains the voltage of the working electrode at the bias potential, Vbias. The reference electrode (RE) potential is compared to the stable input voltage, Vbias. Op-amp U1 generates a voltage at the counter electrode (CE) which is just sufficient to produce a current that is exactly equal and opposite to the working electrode current. At the same time, a constant voltage is maintained by the potentiostat between the reference electrode and working electrode.

Although sensors according to the invention can be used to detect a variety of free radicals, through control of the applied working electrode bias (Vbias), such as a reduction potential, particular free radical species can be identified. For example, hydrogen peroxide can be identified by sweeping the working electrode potential and detecting a signal spike near 100 to 300 mV working potential with respect to the Ag/AgCl reference electrode 130.

Figure 2:
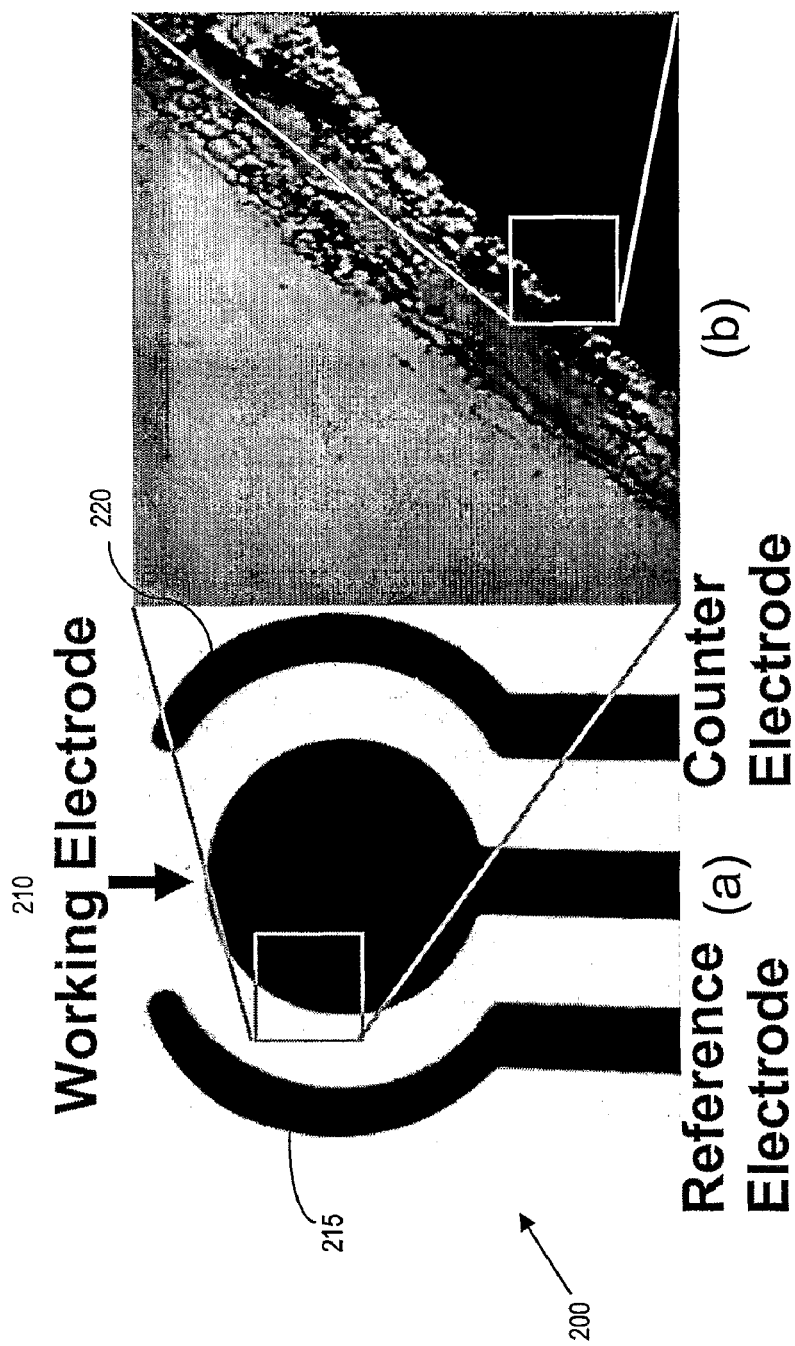
FIG. 2(a) shows an integrated free radical sensor according to another embodiment of the invention. The working electrode is coated with a layer of cerium oxide nanoparticles and is in a layout where the working electrode is surrounded by both a reference electrode and a counter electrode.
FIG. 2(b) is a scanned transmission electron microscopy (TEM) image of the cerium oxide nanoparticle coated working electrode shown in FIG. 2(a).

Free radical sensors according to the invention can be integrated circuit-based sensors formed using conventional integrated circuit techniques. FIG. 2(a) shows a scanned image of an exemplary integrated free radical sensor 200 according to another embodiment of the invention. The working electrode 210 is coated with a layer of cerium oxide nanoparticles according to the invention and is in a layout wherein the working electrode is surrounded by both a reference electrode 215 and a counter electrode 220. FIG. 2(b) shows a scanned TEM image of the cerium oxide nanoparticle coated working electrode 210 shown in FIG. 2(a).

The respective sensor components comprising sensor 200 are can be formed on an integrated circuit compatible substrate, such as a Si substrate using a conventional integrated circuit processing steps, such as lithography, etching, and deposition processing. Using integrated circuit processing, related electronics can be formed on the same chip, such as potentiostats, filters, amplifiers, A/D converters, microprocessors, and a wireless transmitters and optional on-chip antenna, if desired. In one embodiment of the invention, sensors according to the invention are embedded in a subject to be studied in vivo. In this embodiment, a battery is also generally implanted with the sensor chip to supply power to the sensor and related electronics.

Moreover, in the integrated sensor embodiment, other sensors, including conventional sensors, can be formed on the same chip, to sense other materials. Since the sensor is generally based on a planar form factor, other microelectrodes can be formed in chip for electrochemical detection of other chemical species, including oxygen, and carbon dioxide, as well as for pH sensing.

Figure 3:
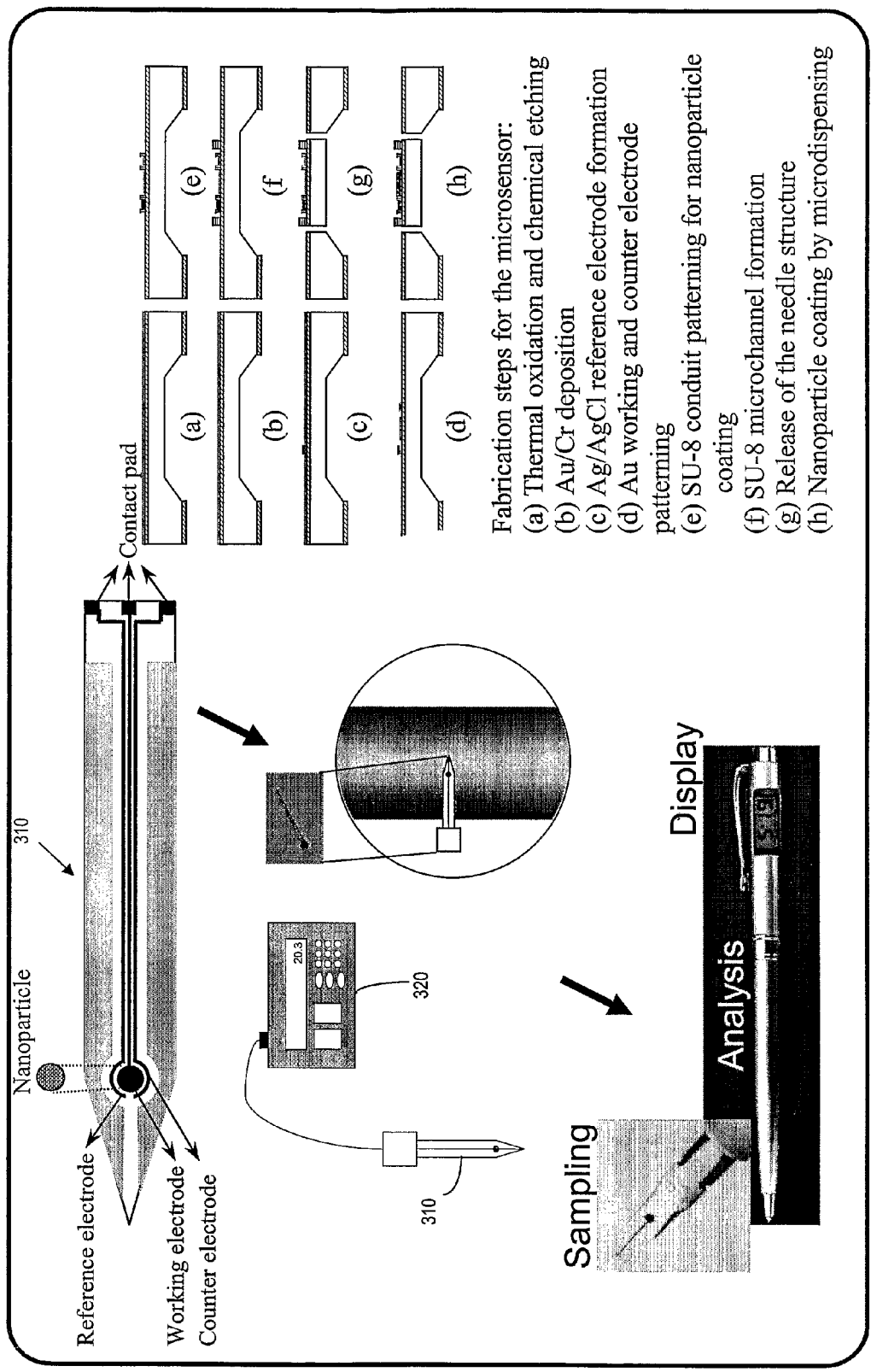
FIG. 3 lists exemplary fabrication steps for forming a releasable integrated free radical microsensor according to an embodiment of the invention.

The right side of FIG. 3 lists fabrication steps (a) through (h) for fabrication of a releasable microsensor according to the invention and shows accompanying cross sectional views. In step (a), thermal oxidation and chemical etching are used. In step (b), Au on Cr (Au/Cr) is deposited on the wafer surface. In step (c), a Ag/AgCl reference electrode is formed. The Au working and counter electrodes are patterned using lithography in step (d). In step (e), a photoresist, such as a negative-tone photoresist UV-sensitive polymer for forming high aspect ratio structure is used, such as SU-8, for patterning for nanoparticle coating occurs SU-8 microchannel formation then occurs in step (f). The microchannel is formed above the substrate the channel walls enclose the WE, CE and RE from outside. The microchannel is generally 1 to 100 µm deep and in one embodiment extends to a needle-like point. Using an etch step in step (g), the integrated microsensor needle shaped structure is released. In step (h), the working electrode is coated with cerium oxide nanoparticles according to the invention preferably using a process comprising microdispensing. Other processes which may be used include microcasting using a microchannel and screen printing. A syringe can also be used to apply a cerium oxide nanoparticle precursor such as described above to the working electrode surface that upon drying adheres to the surface. Alternatively, it is possible to apply the cerium oxide nanoparticles prior to the release step.

Integrated microsensor 310 is shown in the upper left portion of FIG. 3. Contact pads are provide for each of the respective (Reference, Working and Counter) electrodes. Below integrated microsensor 310 is an exemplary potentiostat system 320 including a digital readout electrically coupled to integrated microsensor 310 using respective contact pads shown.

Upon insertion for in vivo use, for example, the target tissue contacts and encloses the needle tip of the microsensor 310. As a result, the fluid associated with the target tissue is drawn into the microchannel of the microsensor by capillary action.

Sensors according to the invention are expected to have numerous commercial applications. Applications in biological and clinical fields include study of age related disorders, such as Alzheimer's and Parkinson's disease, and programmed cell death in cell cultures and plants. As noted above, sensors according to the invention can be implanted for in vivo applications. Applications in the pharmaceutical and food industry include development of drugs for free radical pathogens, and food quality control programs by providing a primary preventive function in free radical generation. Free radicals are generated in various pathogens. Using free radical sensors according to the invention, the concentration of free radicals in such pathogens can be measured to permit study of the effectiveness of different drugs in decreasing the free radicals in those pathogens.

Moreover, for virtually all degenerative disease, chemicals derived from fruit and vegetables have been found to be beneficial. Processes have been created for extract such chemicals from fruits and vegetables to concentrate them in powdered form or in capsules. Current processes, such as pasteurization are known to reduce the effectiveness of such concentrated forms. Free radical sensors according to the invention can be used to speed process development in the food industry damage materials.

EXAMPLES

The present invention is further illustrated by the following specific Example, which should not be construed as limiting the scope or content of the invention in any way.

Figure 4:
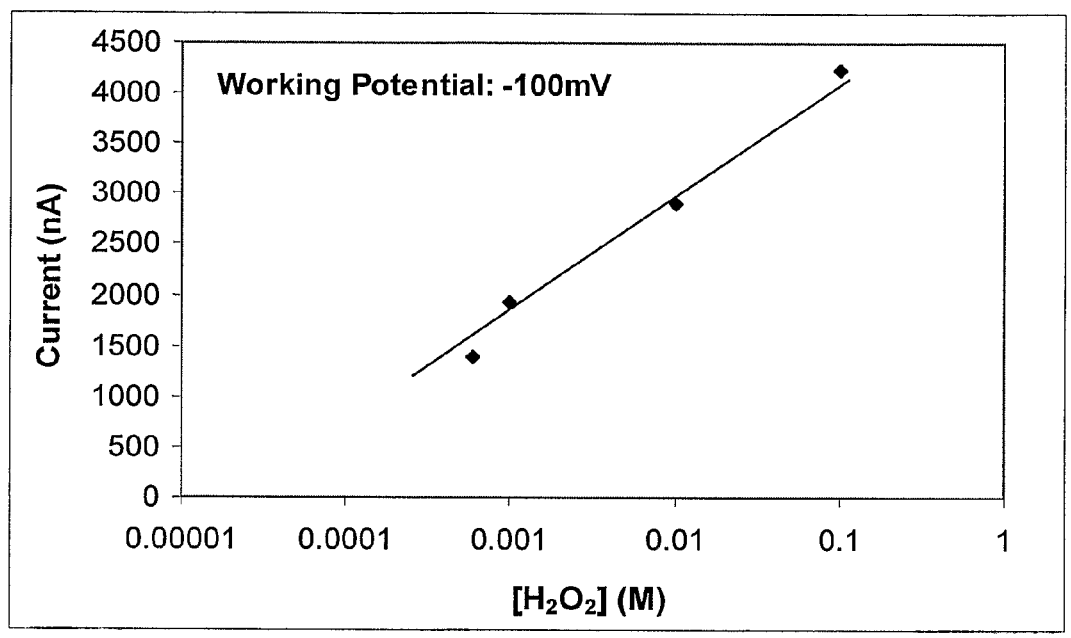
FIG. 4 shows a plot of detected current (nA) using a free radical sensor including a cerium oxide nanoparticle coated working electrode according to an embodiment of the invention coupled to a potentiostat as a function of log concentration of $H_2O_2$. The working potential was −100 mV. A substantially linear response over a wide detection range is demonstrated.

FIG. 4 shows a plot of detected current (nA) using a using a free radical sensor including a cerium oxide nanoparticle coated working electrode according to an embodiment of the invention coupled to a potentiostat as a function of log concentration of $H_2O_2$. The working potential was −100 mV. The results shown demonstrate a substantially linear relationship with increasing signal with increasing log $H_2O_2$ concentration. A wide detection range of over 3 orders of magnitude in hydrogen peroxide concentration is demonstrated.

This invention can be embodied in other forms without departing from the spirit or essential attributes thereof and, accordingly, reference should be had to the following claims rather than the foregoing specification as indicating the scope of the invention.

We claim:

1. An electrochemical sensor system for sensing free radicals or materials which generate free radicals in solution, comprising:
   a working electrode, said working electrode having a coating layer thereon comprising a plurality of cerium oxide nanoparticles;
   a counter electrode, wherein a solution to be analyzed provides electrolytes to electrically couple said working electrode to said counter electrode, and
   electronics electrically coupled to at least one of said working and said counter electrode for measuring and amplifying an electrical current signal generated by reduction or oxidation occurring at said working electrode,
   wherein an average size of said cerium oxide nanoparticles is between 1 and 20 nm.

2. The system of claim 1, wherein an average size of said cerium oxide nanoparticles is between 2 and 10 nm.

3. The system of claim 2, wherein said average size is between 2 and 8 nm.

4. The system of claim 1, wherein a thickness of said coating layer is between 40 nm and 1 μm.

5. The system of claim 1, wherein said coating layer is porous.

6. The system of claim 1, wherein said cerium oxide nanoparticles are doped with at least one trivalent element.

7. The system of claim 6, where said trivalent element comprises La or Nd.

8. The sensor of claim 1, further comprising an integrated circuit substrate, wherein said sensor is a MEMS sensor formed on said integrated circuit substrate.

9. The sensor of claim 8, wherein said substrate comprises silicon.

10. The sensor of claim 8, wherein said electronics comprises a potentiostat disposed on said substrate coupled to said electrodes.

11. An electrode for sensing free radicals or materials which generate free radicals in solution, comprising:
   an electrically conducting core material, said core having a coating layer thereon comprising a plurality of cerium oxide nanoparticles having an average size of between 1 and 20 nm.

12. The electrode of claim 11, wherein said cerium oxide nanoparticles are doped with at least one trivalent element.

13. A method of sensing free radicals, comprising the steps of:
   providing a sensor electrode for sensing free radicals or materials which generate free radicals in solution, comprising an electrically conducting core material, said core having a coating layer thereon comprising a plurality of cerium oxide nanoparticles having an average size of between 1 and 20 nm; and
   positioning said sensor electrode proximate to a solution or medium having an associated solution to be analyzed, said sensor electrode electrically coupled to a counter electrode;
   measuring an electrical current signal generated by reduction or oxidation occurring at said sensor electrode, and
   determining a presence of free radicals in said solution or said medium based on said current signal.

14. The method of claim 13, wherein said medium comprises human tissue.

15. The method of claim 13, wherein said material comprises hydrogen peroxide.

16. The method of claim 15, further comprising the step of determining a concentration of said hydrogen peroxide based on said current signal.

* * * * *